United States Patent
Cabelka et al.

(10) Patent No.: US 9,630,018 B2
(45) Date of Patent: Apr. 25, 2017

(54) CHARGE CONTROL FOR HIGH VOLTAGE THERAPY ENERGY STORAGE COMPONENT

(75) Inventors: Lonny V. Cabelka, Tempe, AZ (US); Mark A. Maass, Tempe, AZ (US)

(73) Assignee: Medtronic, Inc., Minneapolis, MN (US)

( * ) Notice: Subject to any disclaimer, the term of this patent is extended or adjusted under 35 U.S.C. 154(b) by 806 days.

(21) Appl. No.: 13/476,127

(22) Filed: May 21, 2012

(65) Prior Publication Data

US 2013/0197596 A1 Aug. 1, 2013

Related U.S. Application Data

(60) Provisional application No. 61/592,711, filed on Jan. 31, 2012.

(51) Int. Cl.
*A61N 1/378* (2006.01)
*A61N 1/39* (2006.01)
*A61N 1/372* (2006.01)

(52) U.S. Cl.
CPC ........... *A61N 1/3981* (2013.01); *A61N 1/378* (2013.01); *A61N 1/3787* (2013.01); *A61N 1/37276* (2013.01); *A61N 1/3925* (2013.01); *A61N 1/3975* (2013.01)

(58) Field of Classification Search
CPC .. A61N 1/3981; A61N 1/3975; A61N 1/3925; A61N 1/37276; A61N 1/378; A61N 1/3787
USPC .................................. 607/6, 2, 9, 33, 34, 61
See application file for complete search history.

(56) References Cited

U.S. PATENT DOCUMENTS

| | | |
|---|---|---|
| 4,233,659 A | 11/1980 | Pirkle |
| 4,394,719 A | 7/1983 | Moberg |
| 5,285,779 A | 2/1994 | Cameron et al. |
| 5,447,522 A | 9/1995 | Chang et al. |
| 5,458,621 A | 10/1995 | White et al. |
| 5,662,694 A | 9/1997 | Lidman et al. |
| 6,005,370 A | 12/1999 | Gustavson et al. |
| 6,243,604 B1 | 6/2001 | Garrett |
| 6,426,628 B1 | 7/2002 | Palm et al. |
| 6,522,920 B2 | 2/2003 | Silvian et al. |
| 6,549,807 B1 | 4/2003 | Kroll |

(Continued)

*Primary Examiner* — Michael Carey
(74) *Attorney, Agent, or Firm* — Michael J. Ostrom

(57) ABSTRACT

Techniques for controlling charging of a high voltage therapy energy storage component are provided to reduce any undesirable impact from charging during unusual operating conditions. Unusual operating conditions may be caused by any of a number of external factors, including saturation of charging transformer core, circuit failures, capacitor mismatches, or the like, which may result in an unexpected power supply voltage drop or abnormally high currents through device components. An implantable medical device may comprise a power source, a therapy module that includes at least one energy storage component, and a charging module coupled between the power source and the therapy module. The charging module is configured to obtain a measurement representative of an average power drawn from the power source and to terminate charging of the at least one energy storage component based at least on the measurement representative of an average power drawn from the power source.

8 Claims, 6 Drawing Sheets

(56) References Cited

U.S. PATENT DOCUMENTS

| | | |
|---|---|---|
| 6,778,365 B2 * | 8/2004 | Mulhauser ............... 361/18 |
| 6,799,070 B2 | 9/2004 | Wolfe et al. |
| 6,839,590 B2 * | 1/2005 | Waltman .................. 607/5 |
| 6,885,894 B2 | 4/2005 | Stessman |
| 6,892,096 B2 | 5/2005 | Lyden |
| 7,235,050 B2 * | 6/2007 | Schulman et al. ........... 600/300 |
| 7,509,167 B2 * | 3/2009 | Stessman .................. 607/9 |
| 7,579,818 B2 | 8/2009 | Ball et al. |
| 7,619,394 B2 | 11/2009 | Pai et al. |
| 7,656,133 B2 | 2/2010 | Pai et al. |
| 2001/0026146 A1 | 10/2001 | Wuzik et al. |
| 2003/0078620 A1 | 4/2003 | Waltman |
| 2004/0176817 A1 | 9/2004 | Wahlstrand et al. |
| 2005/0088145 A1 | 4/2005 | Loch |
| 2005/0143782 A1 | 6/2005 | Stessman |
| 2006/0022645 A1 | 2/2006 | Bowers |
| 2007/0150019 A1 | 6/2007 | Youker et al. |
| 2007/0179548 A1 | 8/2007 | Armstrong et al. |
| 2007/0255354 A1 | 11/2007 | Wahlstrand et al. |
| 2008/0071168 A1 | 3/2008 | Gauglitz et al. |
| 2008/0097544 A1 | 4/2008 | Gandhi et al. |
| 2008/0183247 A1 | 7/2008 | Harding |
| 2009/0273318 A1 | 11/2009 | Rondoni et al. |
| 2009/0273349 A1 | 11/2009 | Rondoni et al. |
| 2010/0023084 A1 | 1/2010 | Gunderson |
| 2010/0114241 A1 | 5/2010 | Donofrio et al. |
| 2010/0301803 A1 | 12/2010 | Flemming |
| 2011/0077720 A1 | 3/2011 | Torgerson et al. |
| 2011/0148365 A1 * | 6/2011 | Doerr .............. A61N 1/08 320/162 |
| 2012/0157755 A1 * | 6/2012 | D'Ambrosio ....... A61M 1/1086 600/16 |

* cited by examiner

CHARGE CONTROL FOR HIGH VOLTAGE THERAPY ENERGY STORAGE COMPONENT

This application claims the benefit of U.S. Provisional Application No. 61/592,711, filed on Jan. 31, 2012, the content of which is incorporated herein by reference in its entirety.

TECHNICAL FIELD

This disclosure relates generally to implantable medical systems. More particularly, this disclosure describes techniques for controlling charging of a high voltage therapy energy storage component.

BACKGROUND

A wide variety of implantable medical devices that deliver a therapy or monitor a physiologic condition of a patient have been clinically implanted or proposed for clinical implantation in patients. Many of these implantable medical devices rely on an energy storage component, such as a capacitor, to store energy and supply the energy to the patient in form of electrical stimulation therapy. In the case of defibrillation therapy, the implantable medical device may generate a relatively high voltage pulse or series of pulses to a patient suffering from tachyarrhythmia.

Due to the nature of defibrillation therapy or other high voltage therapy, it is not practical for the implantable medical device to supply the energy upon instantaneous demand by drawing from the power source. In other words, a battery or other power source of the implantable medical device is not capable of providing such energy instantaneously. Instead, energy from the power source is accumulated over a certain period of time in one or more defibrillator capacitors which are later discharged to deliver the desired defibrillation therapy. It is desirable that components of the implantable medical device are not unexpectedly stressed during unusual operating conditions.

SUMMARY

This disclosure provides techniques for controlling charging of a high voltage therapy energy storage component to reduce any undesirable impact from charging during unusual operating conditions. Unusual operating conditions may be caused by any of a number of external factors, including saturation of charging transformer core, circuit failures, capacitor mismatches, or the like. These unusual operating conditions may result an unexpected power supply voltage drop or unusually high currents through one or more components.

In one example, this disclosure is directed to an implantable medical system comprising a power source, a therapy module that includes at least one energy storage component, and a charging module coupled between the power source and the therapy module. The charging module is configured to obtain a measurement representative of an average power drawn from the power source over a predetermined period of time and to terminate charging of the at least one energy storage component based at least on the measurement representative of an average power drawn from the power source.

In another example, this disclosure is directed to a method of controlling charging of at least one energy storage component of a therapy module of an implantable medical device. The method comprises obtaining a measurement representative of an average power drawn from a power source of the implantable medical device and terminating charging of the at least one energy storage component based at least on the measurement representative of an average power drawn from the power source.

In a further example, this disclosure is directed to a non-transitory computer-readable medium comprising instructions that, when executed, cause an implantable medical device to obtain a measurement representative of an average power drawn from a power source of the implantable medical device and terminate charging of the at least one energy storage component based at least on the measurement representative of an average power drawn from the power source.

This summary is intended to provide an overview of the subject matter described in this disclosure. It is not intended to provide an exclusive or exhaustive explanation of the techniques as described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

Figure 1:
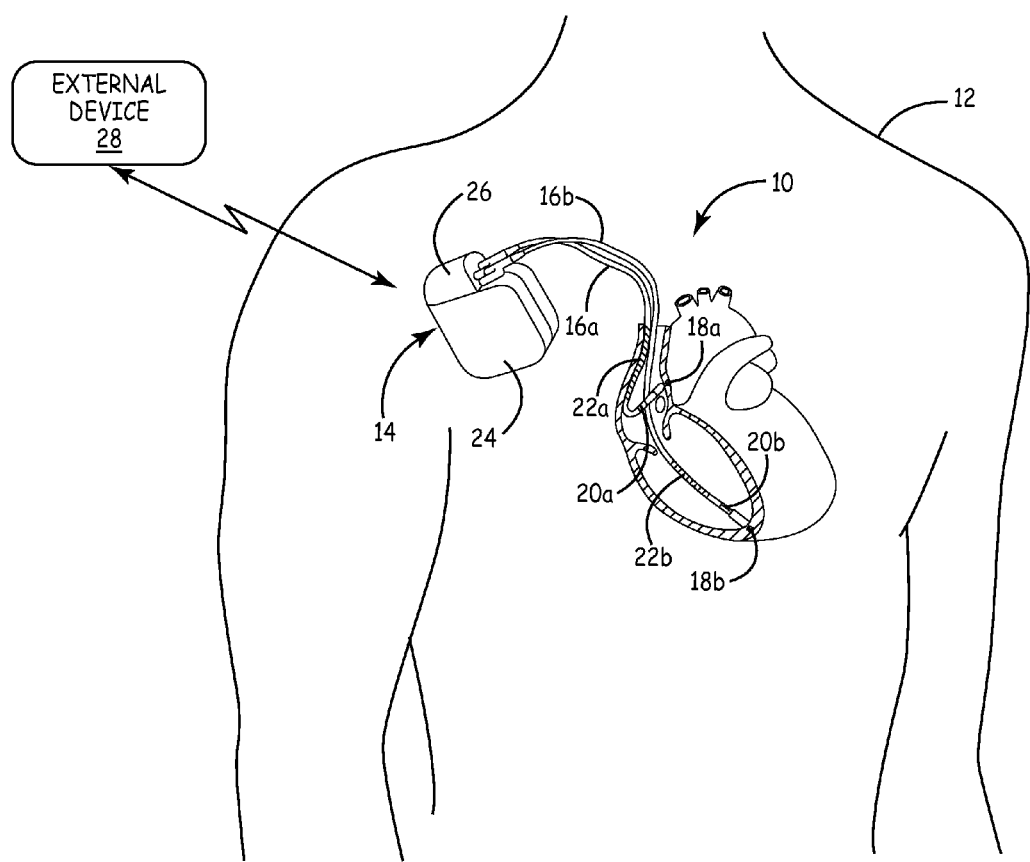
FIG. 1 is a conceptual diagram illustrating an example implantable medical system.

FIG. 1 is a conceptual diagram illustrating an example implantable medical system 10. Implantable medical system 10 includes an IMD 14 connected to one or more leads. In the example illustrated in FIG. 1, IMD 14 is connected to two leads 16a,b implanted within a heart of patient 12 to provide electrical stimulation therapy to the heart. For example, IMD 14 may be an implantable cardioverter defibrillator (ICD), cardiac resynchronization therapy defibrillator (CRT-D), or an implantable cardioverter device. Although described throughout this disclosure in the context of implantable cardiac systems, the techniques of this disclosure may be used in other implantable devices that include an inductor susceptible to saturation in a magnetic field. Additionally, the techniques can be used within the context of external devices, such as external defibrillators.

The configuration of implantable medical system 10 illustrated in FIG. 1 is merely an example. In other examples, implantable medical system 10 may include more or fewer leads extending from IMD 14. For example, IMD 14 may be coupled to three leads, e.g., a third lead implanted within a left ventricle of the heart of the patient. In another example, IMD 14 may be coupled to a single lead that is implanted within either an atrium or ventricle of the heart of the patient. As such, IMD 14 may be used for single chamber or multi-chamber cardiac rhythm management therapy. In further examples, implantable medical system 10 may include leads that are not implanted within the heart, but instead are implanted subcutaneously.

Leads 16*a,b* each includes one or more electrodes. In the example illustrated in FIG. 1, leads 16*a,b* each include a respective tip electrode 18*a,b*, ring electrode 20*a,b*, and defibrillation electrode 22*a,b* located toward a distal end of their respective leads 16*a,b*. When implanted, tip electrodes 18*a,b*, ring electrodes 20*a,b* and defibrillation electrodes 22*a,b* are placed relative to or in a selected tissue, muscle, nerve or other location within the patient 12. Defibrillation electrodes 22*a,b* are elongated electrodes, which, in some instances, may take the form of a coil. Leads 16*a,b* may include more or fewer electrodes than shown in FIG. 1. As one example, one or both of leads 16*a,b* may include a plurality of defibrillation electrodes, such as a right ventricular (RV) defibrillation electrode and a superior vena cava (SVC) defibrillation electrode. The configuration of electrodes, e.g., location, size, shape or the like, may vary based on the target implant location, type of disorder being treated, or the like.

Leads 16*a,b* are connected at a proximal end to IMD 14. IMD 14 illustrated in FIG. 1 includes a housing 24 within which electrical components and a power source of IMD 14 are housed. Housing 24 can be formed from conductive materials, non-conductive materials or a combination thereof IMD 14 and/or housing 24 may include a connector block 26 configured to couple to leads 16*a,b*. Connector block 26 may include one or more receptacles that interconnect with one or more connector terminals located on the proximal end of leads 16*a,b*. Leads 16*a,b* are ultimately electrically connected to one or more of the electrical components within housing 24. One or more conductors (not shown in FIG. 1) extend within leads 16*a,b* from connector block 26 along the length of the lead to engage tip electrode 18*a,b*, ring electrode 20*a,b* and defibrillation electrode 22*a, b*. In this manner, each of tip electrodes 18*a,b*, ring electrodes 20*a,b* and defibrillation electrodes 22*a,b* is electrically coupled to a respective conductor within its associated lead bodies. The respective conductors may electrically couple to electrical circuitry, such as a therapy module or a sensing module, of IMD 14 via connections in connector block 26.

As indicated above, housing 24 encloses a power source and electrical components of IMD 14, such as one or more processors, memories, transmitters, receivers, transceivers, sensors, sensing circuitry, charging circuitry, therapy circuitry, antennas, and/or other components. In the case of an implantable cardiac system, IMD 14 may receive electrical signals corresponding to electrical activity of the heart sensed using different electrode configurations and may process the electrical signals to identify an arrhythmia of the heart. In response to detecting an arrhythmia, IMD 14 selects a programmed therapy to treat the arrhythmia, e.g., pacing and/or defibrillation, and delivers the therapy to the heart via the electrical conductors and one or more of electrodes 18*a,b*, 20*a,b* or 22*a,b*. In the case of defibrillation therapy, for example, IMD 14 may deliver defibrillation shocks via defibrillation electrodes 22*a,b*.

IMD 14 may communicate with an external device 28 to exchange data with external device 28. External device 28 may communicate with IMD 14 to configure IMD 14 to operate within a particular operating mode. For example, communications received from external device 28 may include one or more operating parameters for operation of IMD 14. IMD 14 may also transmit sensed physiological data, diagnostic determinations made based on the sensed physiological data, IMD performance data and/or IMD integrity data to external device 28. IMD 14 and external device 28 may communicate via wireless communication using any techniques known in the art. Examples of communication techniques may include, for example, inductive telemetry or RF telemetry, although other techniques are also contemplated.

Figure 2:
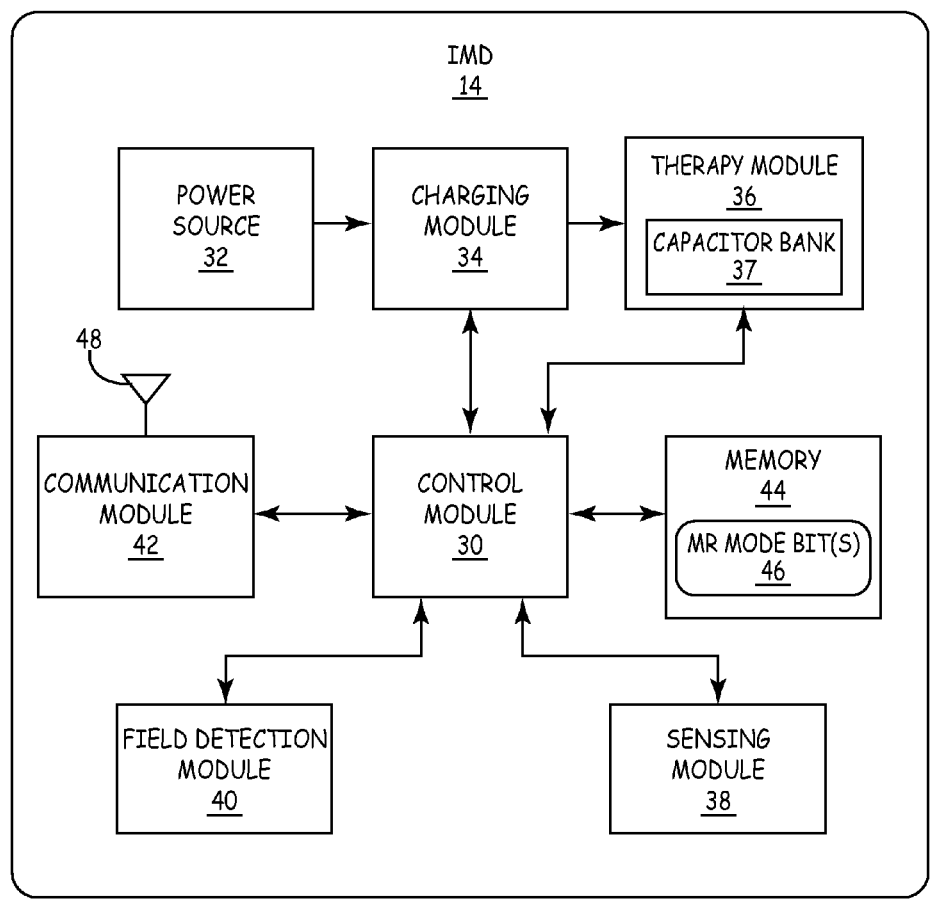
FIG. 2 is a functional block diagram of an example configuration of electronic components of an implantable medical device.

FIG. 2 is a functional block diagram of an example configuration of electronic components of IMD 14. IMD 14 includes a control module 30, charging module 34, therapy module 36, sensing module 38, field detection module 40, communication module 42, and memory 44. The various modules receive power from a power source 32, which may, for example, be a rechargeable or non-rechargeable battery. It should be appreciated that while power source 32 is shown connected only to charging module 34 in the simplified block diagram of FIG. 2, power source 32 also supplies power for all of the active devices of the digital and analog circuitry of IMD 14 and therefore may have other connections to those components.

The configuration of electrical components of IMD 14 illustrated in FIG. 2 is provided merely for purposes of illustration. In other embodiments, IMD 14 may include more or fewer components. Additionally, any of the described modules may be implemented together on a common hardware component or separately as discrete but interoperable hardware, firmware or software components. Depiction of different features as modules is intended to highlight different functional aspects of IMD 14 and does not necessarily imply that such modules or units must be realized by separate hardware, firmware or software components. Rather, functionality associated with one or more modules may be performed by separate hardware, firmware or software components, or integrated within common hardware, firmware or software components.

Sensing module 38 is electrically coupled to some or all of electrodes 18*a,b*, 20*a,b* and 22*a,b* via the conductors of leads 16*a,b*, and/or to a housing electrode (e.g., formed from or on housing 24) via conductors internal to housing 24. Sensing module 38 is configured to obtain signals sensed via one or more of electrodes 18*a,b*, 20*a,b* or 22*a,b* or the housing electrode. Control module 30 may select the electrodes that function as sense electrodes, sometimes referred to as a sensing configuration or sensing vector, in order to monitor electrical activity of the heart. In one example, sensing module 38 may include a switch module that control module 30 may configure to select which of the available electrodes to use for sensing the electrical activity of the heart.

Sensing module 38 may include sensing components used to process signals received from electrodes 18*a,b*, 20*a,b* or 22*a,b*. The components of sensing module 38 may be analog components, digital components or a combination thereof Sensing module 38 may include one or more sense amplifiers, filters, rectifiers, threshold detectors, analog-to-digital converters (ADCs) or the like. Sensing module 38 may include multiple sensing channels each having associated sensing components or one or more sensing channels may share one or more common sensing components. Sensing module 38 may, in some instances, be coupled to one or more other sensors that may or may not be included on leads 16a,b, e.g., via a wired or wireless coupling. Such sensors may include pressure sensors, accelerometers, flow sensors, blood chemistry sensors, activity sensors, magnetic field sensors or other types of physiological sensors.

Control module 30 may process the signals from sensing module 38 to monitor electrical activity of the heart of patient 12. For example, control module 30 may analyze the signals from sensing module 38 to monitor a rate, rhythm and/or morphology of the sensed signals to determine whether patient 12 is experiencing an arrhythmia. In some instances, control module 30 may even distinguish among various types of arrhythmias, e.g., a fast normal rhythm, ventricular tachycardia, or ventricular fibrillation, in accordance with any of the techniques well-known in the field.

Control module 30 may control IMD 14 to generate and deliver electrical stimulation therapy based on the analysis of sensed electrical signals. Therapy module 36 includes a high voltage therapy circuit that includes an energy storage component, illustrated in FIG. 2 as a capacitor bank 37 that includes one or more capacitors. In other instances, therapy module 36 may include energy storage components other than capacitors. Therapy module 36 may also include a switch module for coupling the energy storage component to defibrillation electrodes 22a,b and logic for controlling the coupling of the energy storage component to electrodes 22a,b to create pulses with desired polarities and shapes. In some instances, the switch module of therapy module 36 may be the same switch module used to select electrode combinations for sensing.

In response to detection of a tachyarrhythmia, control module 30 directs charging module 34 to charge capacitor bank 37 of therapy module 36 to desired voltage level. As discussed in further detail herein, charging module 34 may include a transformer that delivers energy from power source 32 to capacitor bank 37 until the voltage across capacitor bank 37 reaches the desired voltage level. When the voltage across capacitor bank 37 reaches the desired level, control module 30 controls therapy module 36 to electrically connect capacitor bank 37 to one or more of defibrillation electrodes 22a,b and thereby deliver of energy stored in capacitor bank 37 as a defibrillation pulse to the heart.

It is desirable that components of the implantable medical device are not unexpectedly stressed during unusual operating conditions. These unusual operating conditions may be caused by any of a number of factors. For example, many implantable medical devices utilize transformers that have a ferromagnetic core in order to achieve a higher inductance value than could otherwise be realized with the same number of turns wound around a non-ferromagnetic core. In the presence of a large magnetic field, such as that generated by an MRI device, the ferromagnetic core may become partially or, in some cases, fully saturated. When partially or fully saturated, the inductance value of the transformer may significantly decrease thereby resulting in a significant change in the impedance presented to power source 32. In particular, the impedance of the load on power source 32 decreases significantly. The significant drop in impedance results in a significant drop in the power supply voltage and an increase in the current flowing through the transformer of charging module 34, which may have adverse consequences to power source 32, charging module 34 and/or therapy module 36. For example, the low power supply voltage and/or the large current drawn from power source 32 may reduce the efficiency or shorten the lifetime of power source 32.

External factors other than a large magnetic field may also result in a significant decrease in the impedance of the load on power source 32 and subsequent increase in current drawn from power source 32. For example, a high voltage capacitor mismatch caused by residual voltage on one of the capacitors of capacitor bank 37 after delivery of therapy or energy dump may result in a decrease in the impedance of the load on power source 32. As another example, failure of one or more circuits within IMD 14 may result in a decrease in the impedance of the load on power source 32. For instance, one or more bits may flip in a memory or hardware register resulting in a switch in charging module 34 being closed for longer than desired. The switch in charging module 34 may also be shorted to ground resulting in an unusually large current draw. Another possible circuit failure may be a fault in a secondary current monitor that is used to determine when to begin charging a primary side of a transformer. Some of these other external factors may be transient whereas other external factors may be permanent. The transient external factors may occur for only a short period of time while others may continue longer. For transient phenomenon the increase in current may present much less of a likelihood of having adverse consequences to power source 32, charging module 34 and/or therapy module 36.

This disclosure describes techniques for controlling charging of high voltage energy storage components to reduce any undesirable impact from charging during unusual operating conditions caused by these external factors. Charging module 34 may, for example, detect a condition indicative of improper charging of capacitor bank 37, determine whether the improper charging is a transient phenomenon and adjust the charging based on whether the improper charging is a transient phenomenon. Such techniques enable charging module 34 to continue to charge capacitor bank 37, albeit at a decreased efficiency, when the improper charging is a transient condition and terminate the charging of capacitor bank 37 when the improper charging is not a transient condition.

As described above, one situation in which the improper charging is not transient occurs when IMD 14 is subject to the large magnetic field of an MRI device. During an MRI procedure, the patient or a particular part of the patient's body is positioned within an MRI device. The MRI device generates a variety of magnetic and electromagnetic fields to obtain the images of the patient, including a static magnetic field, gradient magnetic fields, and radio frequency (RF) fields. The static magnetic field is a large magnetic field that is typically always present around the MRI device whether or not an MRI procedure is in progress. The gradient magnetic fields are pulsed magnetic fields that are typically only present while the MRI procedure is in progress. The RF fields are pulsed high frequency fields that are also typically only present while the MRI procedure is in progress.

The magnitude, frequency or other characteristic of the static magnetic field, gradient magnetic fields and RF fields may vary based on the type of MRI device producing the field or the type of MRI procedure being performed. A 1.5 T MRI device, for example, will produce a static magnetic field of about 1.5 Tesla (T) and have a corresponding RF frequency of about 64 megahertz (MHz) while a 3.0 T MRI device will produce a static magnetic field of about 3.0 Tesla and have a corresponding RF frequency of about 128 MHz. However, other MRI devices may generate fields with different magnitudes, frequencies or other characteristics.

An MRI procedure may take anywhere from several minutes to over an hour. If defibrillation therapy is triggered during an MRI procedure, an abnormally large current may be drawn from power source 32 because of the saturation of the transformer core. Drawing an increased amount of current for such a time period may result in undesirable power consumption, heating of one or more components of IMD 14 or other undesirable effects. As such, it may be desirable to terminate charging of capacitor bank 37 when exposed to an MRI device since charging is not possible when the core of the transformer of the charging module 34 is saturated.

Charging module 34 may therefore be configured to detect a condition indicative of improper charging, to detect a condition indicative of IMD 14 being subjected to fields generated by an MRI device, and to terminate charging when both the condition indicative of improper charging is detected and the condition indicative of IMD 14 being subjected to fields generated by the MRI device is detected. In this manner, charging module 34 may be able to distinguish improper charging caused by transient conditions affecting load impedance (e.g., capacitor mismatch) from improper charging caused by non-transient conditions affecting load impedance (e.g., transformer core saturation caused by large static magnetic field), and adjust charging differently based on whether the condition is transient or non-transient. For example, charging module 34 may adjust the charging algorithm instead of terminating the charging algorithm in instances in which the implantable medical device is charging improperly due to a transient loading condition. As another example, charging module 34 may only adjust the charging algorithm when the implantable medical device is charging improperly due to a non-transient loading condition.

Charging module 34 may measure a current drawn from power source 32 or a voltage of power source 32 and detect the condition indicative of improper charging based on at least the measured current or voltage. Charging module 34 may detect the condition indicative of improper charging when the measured current exceeds a threshold current level or the measured voltage falls below a threshold voltage level. Charging module 34 may monitor an instantaneous current or voltage (e.g., based on the most recent measured current or voltage) or an average current or voltage measured over a period of time (e.g., over several current or voltage measurements). In another example, control module 30 may process the measured currents or voltages associated with power source 32 and provide a signal to charging module 34 upon detecting the condition indicative of improper charging.

In response to detecting the condition indicative of improper charging, charging module 34 may determine whether a condition indicative of IMD 14 being subjected to fields generated by an MRI device is detected. In one example, IMD 14 includes a field detection module 40 to detect one or more fields indicative of the MRI device. Field detection module 40 may include any type of sensor or combination of sensors that provides information indicative of the characteristics of the fields in the surrounding environment including, e.g., one or more Hall effect sensors, a reed switch, a magnetic gradient sensor, an antenna, a radiofrequency (RF) sensing device, or other sensors or combination of sensors. The one or more sensors of field detection module 40 monitor for fields having particular characteristics associated with an MRI device or other device or environment of interest, e.g., particular magnetic field strengths, RF frequencies or gradient field characteristics. For instance, charging module 34 may determine that IMD 14 is being subjected to external fields of an MRI device when an output of field detection module 40 indicates existence of a magnetic field having a strength greater than a threshold strength, e.g., greater than 1.0 Tesla. In other instances, charging module 34 may make the determination based on other information from field detection module 40 in addition to or instead of the magnetic field strength. In further examples, control module 30 may analyze the output of field detection module 40 and provide an indication to charging module 34 in response to detecting the condition indicative of IMD 14 being subjected to fields generated by an MRI device.

In some embodiments, IMD 14 may not include a field detection module 40. Instead, IMD 14 may receive, via communication module 42, a communication from an external device (e.g., external device 28 of FIG. 1) indicating that IMD 14 is being exposed to or will soon be exposed to fields of an MRI device. For example, control module 30 may receive a command to switch to an MR conditional operating mode, during which control module 30 may suspend operation of other functionality of IMD 14 or use a different sensor/algorithm to detect cardiac activity of the heart of patient 12. In some instances, an MR mode configuration bit 46 may be set in memory 44 to indicate that the IMD 14 is currently programmed to operate in the MR conditional operating mode. In this case, the communication or command from external device 28 and/or the value of MR mode configuration bit 46 may be considered the condition indicative of IMD 14 being subjected to fields generated by an MRI device.

Communication module 42 includes any suitable hardware, firmware, software or any combination thereof for communicating with another device, such as external device 28, by wireless telemetry. For example, communication module 42 may include appropriate modulation, demodulation, frequency conversion, filtering, and amplifier components for transmission and reception of data with the aid of antenna 48. Antenna 48 may be located within connector block 26 of IMD 14 or within housing 24 of IMD 14. In one example, antenna 48 may be an inductive coil antenna within housing 24 of IMD 14. In another example, antenna 48 may be an RF antenna located within connector block 26 and coupled to communication module 42 via a feedthrough. In a further example, IMD 14 may include both an inductive coil antenna and an RF antenna coupled to communication module 42 or other antenna located within or outside of housing 24.

In another example, charging module 34 may obtain a measurement representative of an average power drawn from the power source monitor the average voltage of power source 32 over a period of time to distinguish between transient conditions affecting load impedance (e.g., capacitor mismatch or possibly flipped bit in memory or hardware register) and non-transient loading conditions (e.g., permanent short of switch to ground). The measurement representative of the average power drawn from the power source may be an average voltage of power source 32 or an average current drawn from power source 32. A decrease in the average voltage of power source 32 below a threshold voltage or an increase in the average current drawn from power source 32 above a threshold current value may be broader indication of improper charging from a non-transient condition.

As described above, the configuration of electrical components of IMD 14 illustrated in FIG. 2 is provided merely for purposes of illustration. In other embodiments, IMD 14 may include more or fewer components. For example, therapy module 36 may include components for providing low voltage electrical therapy, such as pacing therapy, in addition to the components for providing high voltage electrical therapy. For example, therapy module 36 may include pacer timing and control circuitry that controls the basic time intervals associated with modes of pacing such that therapy module 36 delivers pacing therapy to the heart via one or more of electrodes 18a,b and 20a,b according to one or more therapy programs stored in memory 44. Pacer timing and control circuitry may, for example include one or more counters that track/control escape intervals used to time pacing pulses delivered to the atrium and/or ventricle of patient 12. Pacer timing and control circuitry may also include circuitry to control the amplitude, duration, polarity, or other characteristic of the pacing pulses based on input from control module 30 and/or stored therapy program parameters. In some instances, control module 30 may control the pacer timing and control circuitry of therapy module 36 to deliver anti-tachycardia pacing (ATP) prior to delivering the defibrillation shock in an effort to terminate the tachyarrhythmia episode.

The various modules of IMD 14 may include any one or more processors, controllers, digital signal processors (DSPs), application specific integrated circuits (ASICs), field-programmable gate arrays (FPGAs), or equivalent discrete or integrated circuitry, including analog circuitry, digital circuitry, or logic circuitry. Memory 44 may include computer-readable instructions that, when executed by control module 30 or other component of IMD 14, cause one or more components of IMD 14 to perform various functions attributed to those components in this disclosure. Memory 44 may include any volatile, non-volatile, magnetic, optical, or electrical media, such as a random access memory (RAM), read-only memory (ROM), non-volatile RAM (NVRAM), static non-volatile RAM (SRAM), electrically-erasable programmable ROM (EEPROM), flash memory, or any other non-transitory computer-readable storage media.

Figure 3:
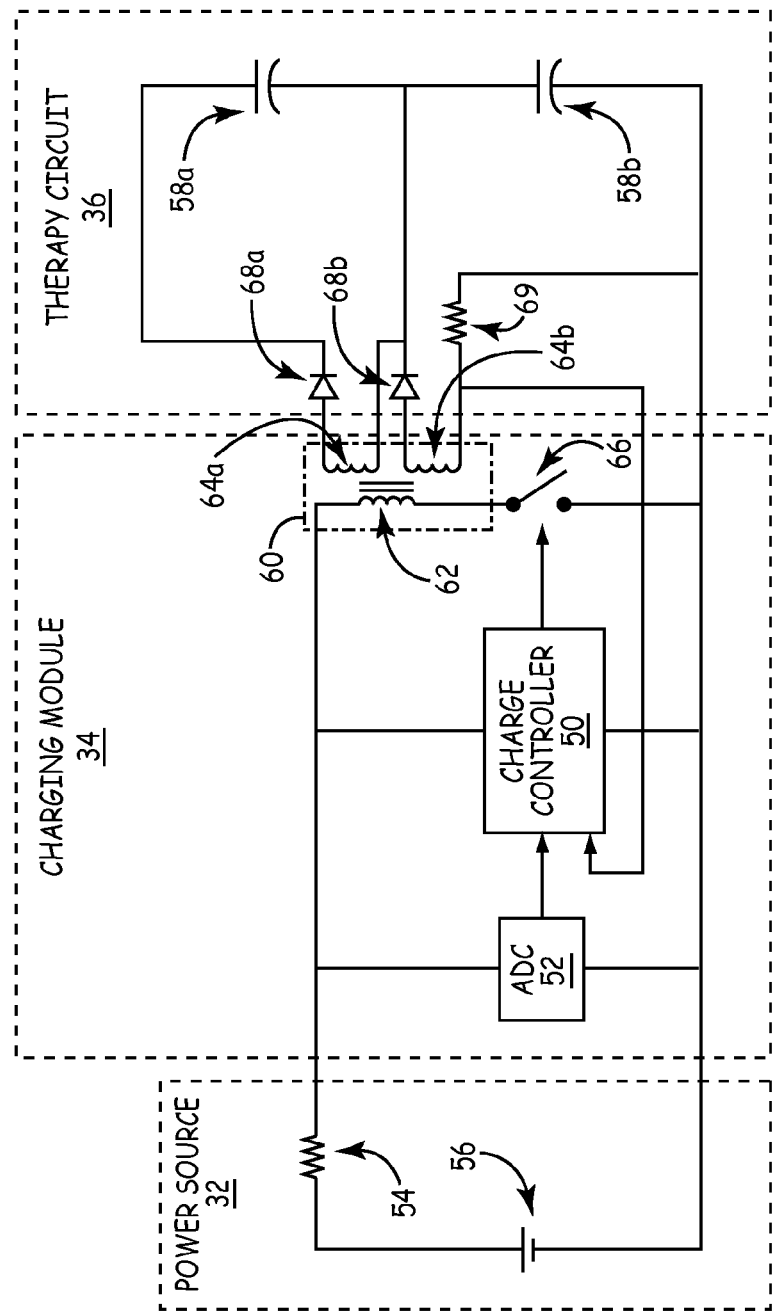
FIG. 3 is a drawing further illustrating further details of example charging module in conjunction with power source and therapy circuit.

FIG. 3 is a drawing further illustrating example charging module 34 in conjunction with power source 32 and therapy circuit 36. Power source 32 of FIG. 3 is represented by a voltage source 56 and an internal equivalent series resistance 54. Internal resistance 54 of a battery is dependent on the size of the battery, the chemical properties of the battery, age of the battery, temperature of the battery and the discharge current of the battery. Internal resistance 54 increases with the age of a battery, but for most battery types ranges from a fraction of an ohm to a few ohms As described above, charging module 34 delivers energy from energy source 32 to capacitor bank 37, represented in FIG. 3 as capacitors 58a and 58b (referred to herein collectively as capacitors 58). Therapy circuit 36 may include more of fewer capacitors 58 or include other types of energy storage components. Energy is delivered from power source 32 to energy-storage capacitors 58 via transformer 60. In the example charging module 34 of FIG. 3, transformer 60 includes a primary coil 62 and two secondary coils 64a and 64b (referred to herein collectively as secondary coils 64) wound around a ferromagnetic core. Primary coil 62 has N turns and secondary coils 64a and 64b have $M_1$ and $M_2$ turns, respectively. The number of turns N, $M_1$ and $M_2$ may vary depending on the desired step-up of the voltage, the types of materials used to construct transformer 60, the types of load or other factors. The number of turns of secondary coils 64 ($M_1$ and $M_2$) may be the same (equal to one another) or different. The number of turns $M_1$ and $M_2$ of secondary coils 64 will typically be larger than the number of turns N of primary coil 62. Although the example transformer 60 illustrated in FIG. 3 includes a single primary coil 62 and two secondary coils 64, transformer 60 may include a different number of primary coils or secondary coils, such as a single secondary coil or more than two secondary coils. Although modeled as an ideal transformer, transformer 60 may have non-ideal characteristics, which may be modeled as additional inductance, capacitance and/or resistance.

In operation, current supplied by power source 32 flows through primary coil 62 of transformer 60 and induces current in secondary coils 64. The current flowing through secondary coils 64 is stored as a potential difference (voltage) across the plates of respective ones of capacitors 58 of capacitor bank 37. Current flow is controlled by a switch 66. Switch 66 may be implemented using a number of types of solid state devices, including any of a number of different types of transistors.

Charge controller 50 controls the state of switch 66 to permit or interrupt the flow of current through primary coil 62. When switch 66 is in a first state, referred to herein as a "closed" state, switch 66 permits current to flow through primary coil 62 of transformer 60, causing energy to be stored in primary coil 62. When switch 66 is in a second state, referred to herein as an "open" state, switch 66 interrupts current flow through primary coil 62 of transformer 60. During the open state the energy stored in primary coil 62 of transformer 60 transfers to secondary coils 64 of transformer 60, thus generating a current on the secondary side of transformer 60. The current induced on secondary coils 64 flows through diodes 68a and 68b (referred to herein collectively as diodes 68) and charges energy-storage capacitors 58. Diodes 68 prevent energy-storage capacitors 58 from discharging the built up voltages. In the case in which switch 66 is a MOSFET, for example, the drain and source terminals of the MOSFET are connected between the primary coil 62 and ground, respectively, while the gate terminal is connected to an output of charge controller 50. Charge controller 50 controls the state of the MOSFET to permit or interrupt the flow of current through primary winding 62 depending on the signal applied to the gate.

During charging, charge controller 50 controls switch 66 to change between the open state and the closed state to provide a series of current pulses to energy-storage capacitors 58, thereby charging energy-storage capacitors 58. Charge controller 50 controls the rate at which switch 66 cycles or is switched between the open state and the closed state to control the rate at which capacitors 58 are charged. Charge controller 50 may monitor the current flowing through the low-side secondary winding 64b, e.g., using resistor 69. Charger controller 50 begins the next primary charge cycle when the secondary current drops to almost zero. Charge controller 50 continues to charge capacitors 58 until a desired voltage is reached across capacitors 58. As such, charge controller 50 may use a potential difference across one or both of capacitors 58 as a feedback parameter to determine when charging is complete.

Charge controller 50 may, in some instances, control the rate at which switch 66 is switched between the open state and the closed state based on one or more feedback parameters, such as a voltage or current measured somewhere within the primary-side of the circuit. Controlling the rate at which switch 66 is switched permits charge controller 50 to control the charging to reduce the likelihood of improper charging conditions that may have adverse consequences on power supply 32 or components of charging module 34. For example, improper charging conditions, such as excessive current draw from power source 32, may reduce the efficiency and/or shorten the lifetime of power supply 32.

During times of high current drawn from power source 32, an increased rate of switching may reduce the amount of time that a large amount of current is drawn from power source 32. During times of low current drawn from power source 32, a decreased rate of switching may increase the amount of time that current is drawn from power source 32 to increase the amount of charge transferred to the secondary coils during the switching cycle.

In one example, charge controller 50 may control the rate at which switch 66 is switched between the open state and the closed state based on a voltage of power source 32. In this case, charge controller 50 receives an input representative of the voltage level of power source 32. Charging module 34 includes voltage measurement module, illustrated in FIG. 3 as an analog-to-digital converter (ADC) 52 that is connected in parallel with power source 32. ADC 52 may periodically measure a voltage of power source 32 and provide the measurement to charge controller 50. ADC 52 may periodically measure the voltage of the battery, e.g., approximately every 2 milliseconds (ms), 3 ms, 4 ms, 5 ms, 6 ms, or other increment. Although illustrated as an ADC 52, charging module 34 may include other components or circuits that measure a voltage representative of a voltage across power source 32.

Charge controller 50 may adjust the rate at which switch 66 is switched between the open and closed state using one or more of the measured voltage values from ADC 52. In some instances, charge controller 50 may adjust the rate at which switch 66 is switched as a function of each of the individual voltage measurements from ADC 52. In other instances, charge controller 50 may adjust the rate at which switch 66 is switched as a function of an average of a plurality of voltage measurements from ADC 52 over a predetermined time. In some situations, charge controller 50 may switch 66 between the open and closed state using a fixed rate not dependent on the measured voltage values.

During some non-transient charging conditions, charging using the adjustable rate techniques may still have adverse consequences on the lifetime of power supply 32. For example, when the ferromagnetic core of transformer 60 becomes saturated in the presence of a large magnetic field, such as that generated by an MRI device, no energy is transferred from primary coil 62 to secondary coils 64. As such, capacitors 58 will not charge regardless of the rate at which switch 66 is switched. Charge controller 50 may identify these non-transient charging conditions and terminate the charging when such conditions exist.

To this end, charge controller 50 may be configured to determine whether IMD 14 is being subjected to fields generated by an MRI device in response to detecting a condition indicative of improper charging, e.g., voltage of power source 32 drops below a threshold voltage value. For example, charge controller 50 may determine IMD 14 is being subjected to fields generated by an MRI device when field detection module 40 detects one or more fields having particular characteristics associated with an MRI device, e.g., particular magnetic field strengths, RF frequencies or gradient field characteristics. In another example, charge controller 50 may analyze a value of MR mode configuration bit 46 to determine whether the condition indicative of IMD 14 being subjected to fields generated by an MRI device exists. In further examples, control module 30 (FIG. 2) may analyze the output of field detection module 40, analyze MR mode configuration bit 46, or receive a command or communication from external device 28 to determine whether IMD 14 is being subjected to fields generated by an MRI device and provide an indication that such a condition is detected to charge controller 50.

If charge controller 50 detects the condition indicative of IMD 14 being subjected to fields generated by an MRI device, charge controller 50 terminates charging. Thus, the determination that IMD 14 is being subjected to fields generated by the MRI device serves as an indication that the charging condition is a non-transient charging condition. If IMD 14 is not being subjected to fields generated by an MRI device while the improper charging condition is detected, charge controller 50 continues charging using the adjustable rate charging techniques described above or a conventional charging technique. In this manner, charge controller 50 may be able to distinguish between transient conditions affecting load impedance (e.g., capacitor mismatch) and non-transient loading conditions caused by IMD 14 being in close proximity to a large magnetic field, e.g., from an MRI device, and adjust charging differently based on whether the condition is transient or non-transient.

In another example, charge controller 50 may monitor the average voltage of power source 32 over a period of time to distinguish between transient conditions affecting load impedance (e.g., capacitor mismatch) and non-transient loading conditions. For example, charge controller 50 may compute the average voltage of power source 32 using a plurality of most recent voltage measurements of ADC 52, such as the five most recent voltage measurements. When ADC 52 measures the voltage of power source 32 approximately every two to six milliseconds as described above, the period of time may be between approximately ten and thirty milliseconds. In any case, the period of time may be less than approximately fifty milliseconds. However, any number of most recent voltage measurements may be used in computing the average voltage. A decrease in the average voltage of power source 32 below a threshold voltage value may be broader indication of improper charging from a non-transient condition. In one example, the threshold voltage value may be a value between approximately 1-2 volts or between approximately 1-1.5V. The average voltage of power source 32 may fall below the threshold voltage value due to non-transient conditions other than core saturation of transformer 60 due to the large magnetic field of the MRI device. Thus, in addition to adjusting the switching cycles of switch 66 based on the individual battery voltage measurements of power source 32, charge controller 50 may terminate the charging when the average voltage of power source 32 falls below a threshold value. This technique may be used alone or in conjunction with the technique that monitors for detection of IMD 14 being subjected to fields generated by the MRI device.

Although charge controller 50 is described as monitoring the output voltage of power source 32 to distinguish between transient and non-transient conditions affecting load impedance, those skilled in the art will appreciate that charge controller 50 may use current measurements instead of voltage measurements. For example, charge controller 50 may monitor a current drawn from power source 32, e.g., by monitoring the amplitude of the current through the primary coil 62 or switch 66, and detect the condition indicative of improper charging when the current drawn from power source 32 increases above a threshold current value. In instances in which charge controller 50 controls charging based on current measurements, charging module 34 may not include ADC 52, but instead include a circuit for measuring current through a portion of the circuit.

Figure 4:
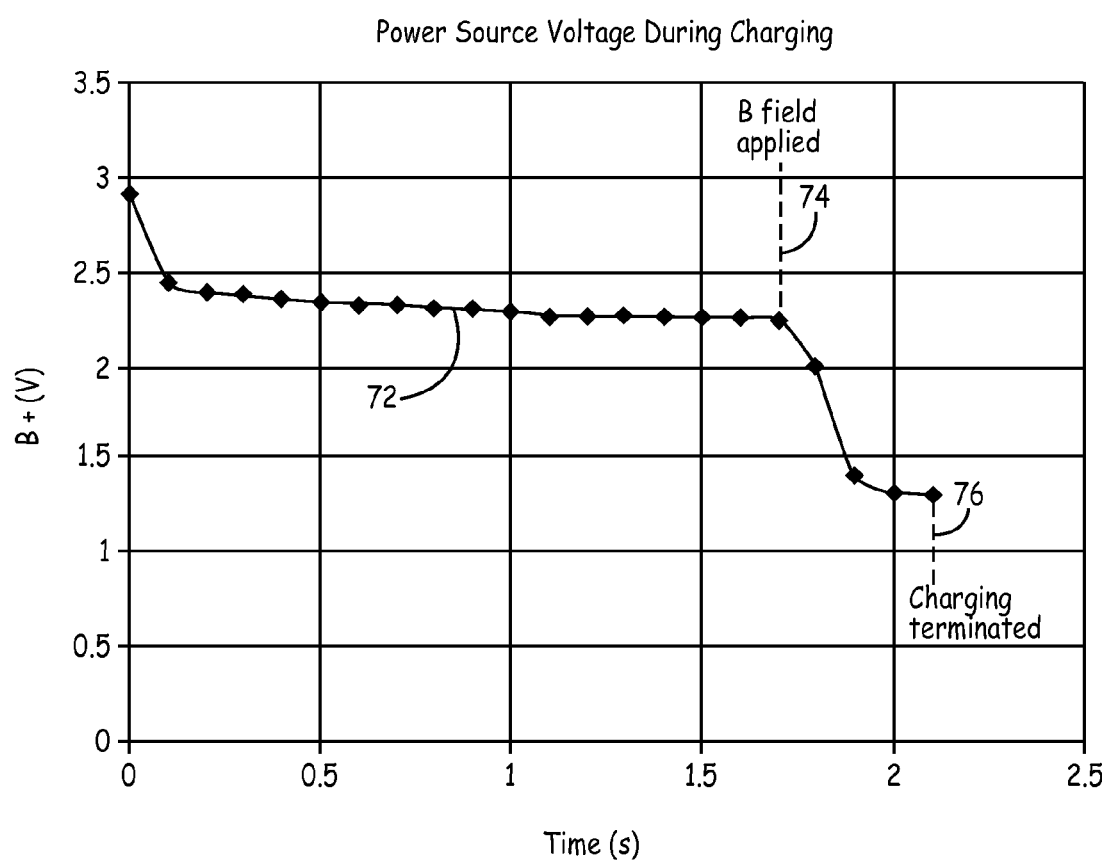
FIG. 4 is a graph illustrating an example plot of a power source voltage during charging.

FIG. 4 is a graph illustrating an example plot 72 of voltage measurements representative of the voltage of power supply 32 during charging. As illustrated in FIG. 4, at the initiation of the charging the voltage of power supply 32 drops to a value between approximately 2.0V and 2.5V. While the voltage of power supply 32 remains within that range the device exhibits proper charging. When a large static magnetic field is applied at approximately point 74, the voltage of power supply 32 drops drastically to a value between approximately 1.0V and 1.5V. Such a voltage of power supply 32 is indicative of improper charging. Charging is terminated at approximately point 76, e.g., upon determining that IMD 14 is being subjected to fields generated by an MRI device or upon an average voltage of power source 32 falling below a threshold value. The values to which the voltage of power supply 32 drops are dependent upon the initial voltage of power supply 32. In one example, the threshold voltage value may be a value between approximately 1-2 volts or between approximately 1-1.5V.

Figure 5:
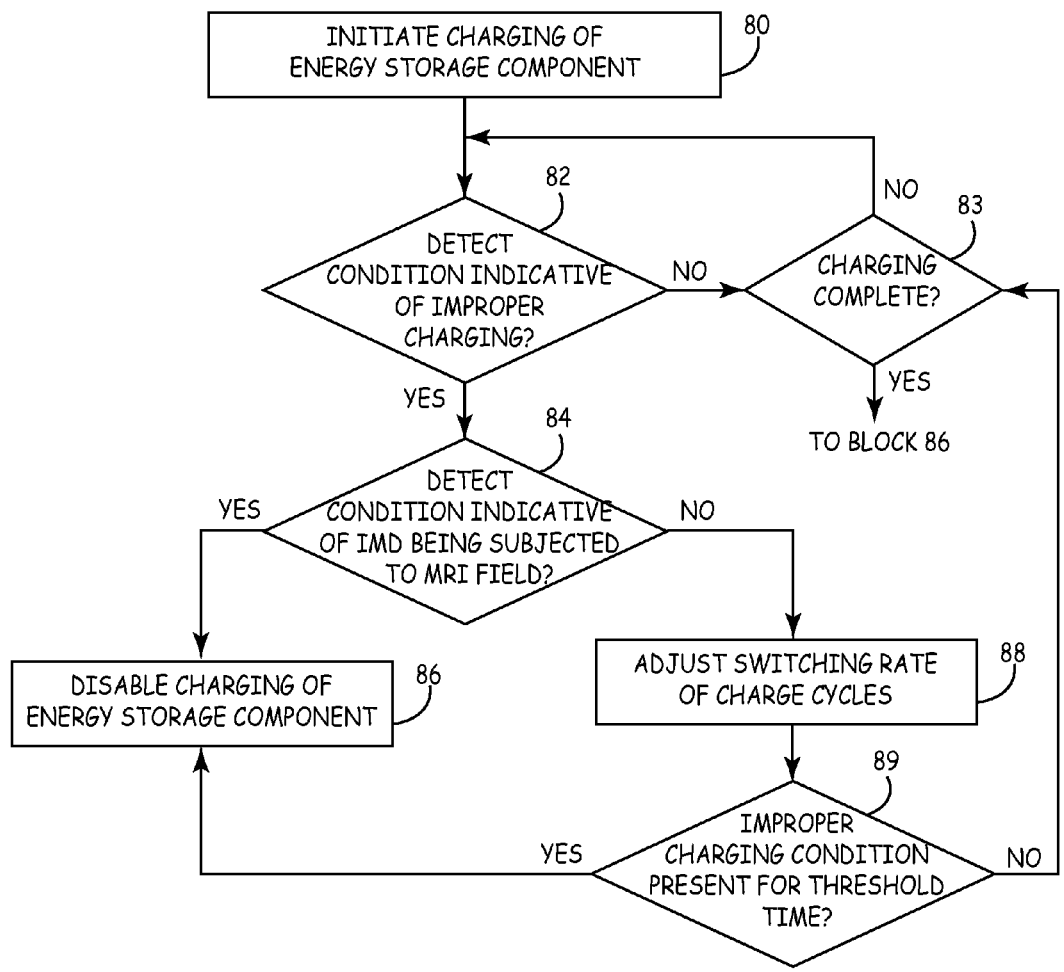
FIG. 5 is a flow diagram illustrating example operation of an implantable medical device controlling charging of a high voltage energy storage component in accordance one of the techniques of this disclosure.

FIG. 5 is a flow diagram illustrating example operation of an implantable medical device controlling charging of a high voltage energy storage component in accordance one of the techniques of this disclosure. Initially, charging module 34 initiates charging of the energy storage component (block 80). For example, control module 30 may direct charging module 34 to charge the energy storage component, e.g., capacitors 58 of capacitor bank 37, in response to detecting a tachyarrhythmia.

Charging module 34 or control module 30 monitors the charging of one or more energy storage components to determine whether a condition indicative of improper charging is detected (block 82). Charging module 34 or control module 30 may, for example, measure a current drawn from power source 32 or a voltage of power source 32 and detect the condition indicative of improper charging based on at least the measured current or voltage. The condition indicative of improper charging may be detected when the measured current exceeds a threshold current level or the measured voltage falls below a threshold voltage level. In one example, the threshold voltage value may be a value between approximately 1-2 volts or between approximately 1-1.5V. Charging module 34 or control module 30 may monitor an instantaneous current or voltage (e.g., based on the most recent measured current or voltage) or an average current or voltage measured over a period of time (e.g., over several current or voltage measurements).

When charging module 34 or control module 30 does not detect the condition indicative of improper charging ("NO" branch of block 82), charging module 34 or control module 30 determines whether charging of the energy storage component is complete (block 83). When charging module 34 determines that charging is complete, e.g., the energy storage component has reached the desired voltage level ("YES" branch of block 83), charging module 34 disables the charging of energy storage component (block 86). When charging module 34 determines that charging is not complete, e.g., the energy storage component has not reached the desired voltage level ("NO" branch of block 83), charging module 34 continues to 36 monitor the charging of the energy storage component(s) to determine whether the condition indicative of improper charging is detected (block 82).

When charging module 34 or control module 30 detects the condition indicative of improper charging ("YES" branch of block 82), charging module 34 or control module 30 determines whether a condition indicative of IMD 14 being subjected to fields generated by an MRI device is detected (block 84). In one example, charging module 34 or control module 30 detect the condition indicative of IMD 14 being subjected to fields generated by an MRI device based on the output of one or more sensors that provide information indicative of the characteristics of the fields in the surrounding environment including, e.g., one or more Hall effect sensors, a reed switch, a magnetic gradient sensor, an antenna, a radiofrequency (RF) sensing device, or other sensors. In another example, charging module 34 or control module 30 detect the condition indicative of IMD 14 being subjected to fields generated by an MRI device based on a value of an MR mode configuration bit 46 or a communication from an external device indicating that IMD 14 is being exposed to or will soon be exposed to fields of an MRI device.

When charging module 34 or control module 30 detects the condition indicative of IMD 14 being subjected to fields generated by an MRI device ("YES" branch of block 84), charging module 34 or control module 30 disables or terminates charging of the energy storage component (block 86). When charging module 34 or control module 30 does not detect the condition indicative of IMD 14 being subjected to fields generated by an MRI device ("NO" branch of block 84), charging module 34 or control module 30 disables or terminates charging of the energy storage component (block 86).

When charging module 34 or control module 30 does not detect the condition indicative of IMD 14 being subjected to fields generated by an MRI device ("NO" branch of block 84), charging module 34 may adjust the switching rate of charge cycles (block 88). Increasing the rate at which switching may reduce the amount of time that a large amount of current is drawn from power source 32. As such, charging of the energy storage component continues albeit at a reduced efficiency.

Charging module 34 or control module 30 determines whether the improper charging condition is present for a threshold period of time (block 89). Charging module 34 or control module 30 may compare an average voltage or current of power source over a predetermined time to a threshold value to determine whether the improper condition is present for a threshold period of time. Alternatively, charging module 34 or control module 30 may initiate a timer upon initially detecting the condition indicative of improper charging and determine that the improper charging condition is present for a threshold period of time upon the timer reaching a predetermined time. The predetermined period of time may be less than approximately fifty milliseconds and, in some instances, between the range of ten and thirty milliseconds. When charging module 34 or control module 30 determines the improper charging condition is present for the threshold period of time ("YES" branch of block 89), charging module 34 or control module 30 disables or terminates charging of the energy storage component (block 86). When charging module 34 or control module 30 determines the improper charging condition has not been present for the threshold period of time ("NO" branch of block 89), charging module 34 or control module 30 determines whether charging of the energy storage component is complete (block 83).

Figure 6:
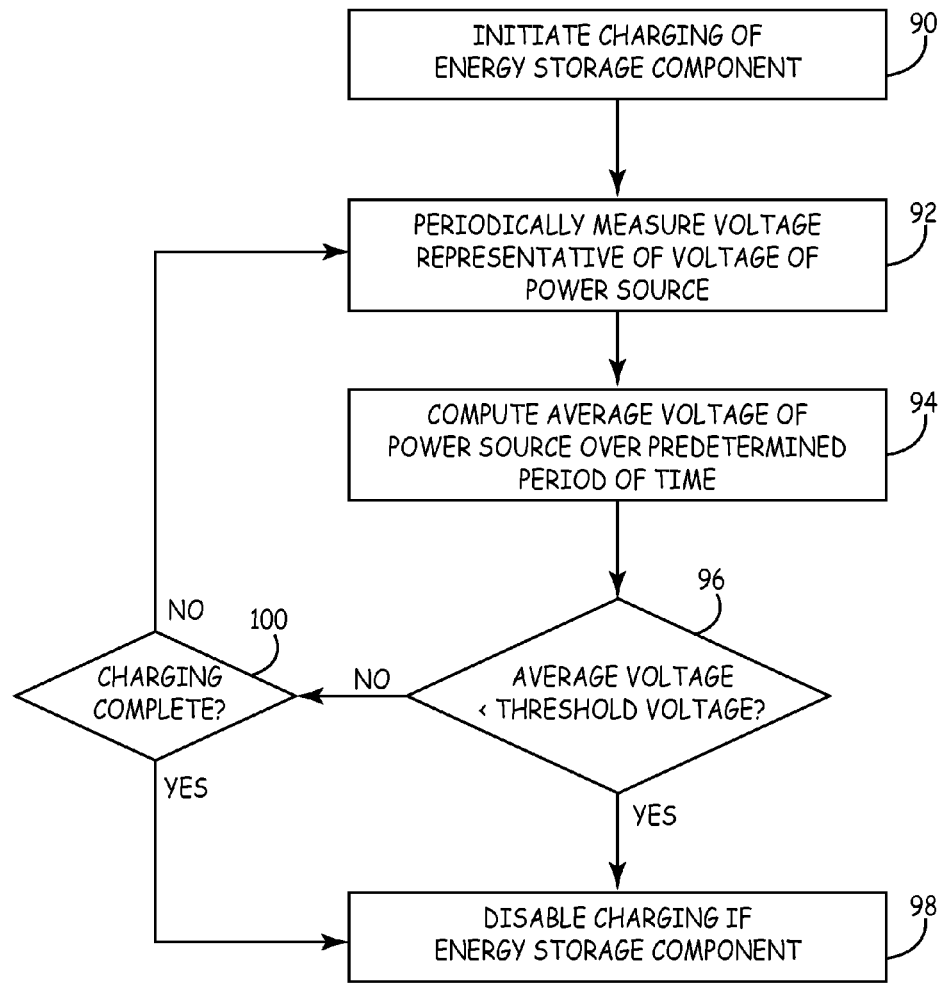
FIG. 6 is a flow diagram illustrating example operation of an implantable medical device controlling charging of a high voltage energy storage component in accordance with another of the techniques of this disclosure.

FIG. 6 is a flow diagram illustrating example operation of an implantable medical device controlling charging of a high voltage energy storage component in accordance with another of the techniques of this disclosure. Initially, charging module 34 initiates charging of the energy storage component (block 90). For example, control module 30 may direct charging module 34 to charge the energy storage component, e.g., capacitors 58 of capacitor bank 37, in response to detecting a tachyarrhythmia.

Charging module 34 periodically measures a voltage representative of voltage of power source 32 (block 92). For example, ADC 52 of charging module 34 may be connected in parallel with power source 32 and periodically measure a voltage of across power source 32. Charging module 34 or control module 30 may compute an average voltage of power source 32 over a period of time (block 94). Charging module 34 or control module 30 may compute an average voltage of power source 32 using a plurality of most recent voltage measurements of ADC 52 over a period of time. For example, charging module 34 may compute the average voltage of power source 32 using the five most recent voltage measurements or the voltage measurements taken in the last 20 ms. Other numbers of voltage measurements or periods of time may be used, however.

Charging module 34 or control module 30 compares the average voltage of power source 32 to a threshold value to determine whether the average voltage of power source 32 is less than the threshold value (block 96). When the average voltage of power source 32 is less than the threshold value ("YES" branch of block 96), charging module 34 or control module 30 disables or terminates charging of the energy storage component (block 98). Such a decrease in the average voltage of power source 32 is an indication of a non-transient improper charging condition.

When the average voltage of power source 32 is not less than the threshold value ("NO" branch of block 96), charging module 34 or control module 30 determines whether charging of the energy storage component is complete (block 100). When charging module 34 determines that charging is complete, e.g., the energy storage component has reached the desired voltage level ("YES" branch of block 100), charging module 34 disables the charging of energy storage component (block 98). When charging module 34 determines that charging is not complete, e.g., the energy storage component has not reached the desired voltage level ("NO" branch of block 100), charging module 34 continues to periodically measure the voltage of power source 32 and compute an updated average voltage (blocks 92 and 94).

Although the flow diagram of FIG. 6 is described in the context of controlling charging as a function of the voltage of the powers source 32, a similar method may control charging as a function of the current drawn from power source 32.

The techniques described in this disclosure, including those attributed to IMD 14, may be implemented, at least in part, in hardware, software, firmware or any combination thereof For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" may generally refer to any of the foregoing circuitry, alone or in combination with other circuitry, or any other equivalent circuitry.

Such hardware, software, or firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a non-transitory computer-readable medium such as RAM, ROM, NVRAM, EEPROM, or flash memory, magnetic data storage media, optical data storage media, or the like. The instructions may be executed to support one or more aspects of the functionality described in this disclosure.

Various examples have been described. These and other examples are within the scope of the following claims.

The invention claimed is:

1. An implantable medical device comprising:
   a power source;
   a therapy module that includes at least one energy storage component;
   a charging module coupled between the power source and the therapy module, wherein the charging module is configured to obtain a measurement representative of an average power drawn from the power source over a predetermined period of time and to terminate charging of the at least one energy storage component based at least on the measurement representative of an average power drawn from the power source.

2. The implantable medical device of claim 1, wherein the measurement representative of the average power drawn from the power source comprises an average voltage of the power source, the charging module being configured to obtain a plurality of voltage measurements representative of a voltage of the power source, compute the average voltage of the power source using the plurality of voltage measurements, compare the average voltage of the power source to a threshold voltage, and terminate charging of the at least one energy storage component when the average voltage of the power source is less than the threshold voltage.

3. The implantable medical device of claim 2, wherein the charging module includes:
   a transformer including at least one primary coil and at least one secondary coil; and
   a switch coupled in series with the transformer, wherein the switch may be configured into a closed state during which current is permitted to flow through the primary coil of the transformer and an open state during which current does not flow through the primary coil of the transformer,
   wherein the charging module is configured to adjust a rate at which the switch switches between the open state and the closed state based on the average voltage when the average voltage of the power source is greater than or equal to the threshold voltage.

4. The implantable medical device of claim 2, wherein the charging module includes:
   a transformer including at least one primary coil and at least one secondary coil; and
   a switch coupled in series with the transformer, wherein the switch may be configured into a closed state during which current is permitted to flow through the primary coil of the transformer and an open state during which current does not flow through the primary coil of the transformer,
   wherein the charging module is configured to adjust a rate at which the switch switches between the open state and the closed state based on a most recent voltage measurement when the average voltage of the power source is greater than or equal to the threshold voltage.

5. The implantable medical device of claim 2, wherein the charging module computes the average voltage of the power source using the plurality of voltage measurements over a period of time that is less than approximately 50 milliseconds.

6. The implantable medical device of claim 1, wherein the measurement representative of the average power drawn from the power source comprises an average current drawn from the power source, the charging module being configured to obtain a plurality of current measurements representative of a current drawn from the power source, compute the average current drawn from the power source using the plurality of current measurements, compare the average current of the power source to a threshold current, and terminate charging of the at least one energy storage component when the average current drawn from the power source is greater than the threshold current.

7. The implantable medical device of claim 1, wherein the energy storage component comprises at least one capacitor.

8. The implantable medical device of claim 1, wherein the therapy module generates defibrillation therapy in response to detecting a tachyarrhythmia.

* * * * *